United States Patent [19]

May

[11] Patent Number: 4,523,338
[45] Date of Patent: Jun. 18, 1985

[54] DEMOUNTABLE JOINT

[75] Inventor: Denis R. W. May, London, England

[73] Assignee: J. E. Hanger & Company Limited, London, England

[21] Appl. No.: 462,244

[22] Filed: Jan. 31, 1983

Related U.S. Application Data

[63] Continuation-in-part of Ser. No. 386,454, Jun. 8, 1982, abandoned.

[30] Foreign Application Priority Data

Jun. 9, 1981 [GB] United Kingdom .............. 8117573
Jun. 9, 1981 [GB] United Kingdom .............. 8117574

[51] Int. Cl.$^3$ .............................................. A61F 1/08
[52] U.S. Cl. ................................................ 3/21; 3/2; 3/12.8; 403/378
[58] Field of Search ................. 403/378, 379, 374; 3/21, 30, 6, 22, 2, 5, 15, 17, 12.8

[56] References Cited

U.S. PATENT DOCUMENTS

| | | | |
|---|---|---|---|
| 1,141,067 | 5/1915 | Lloyd | 273/73 H |
| 1,880,894 | 10/1932 | Dorman | 403/374 |
| 3,258,283 | 6/1966 | Winberg et al. | 403/379 |
| 3,422,684 | 1/1969 | Finnieston | 3/21 |
| 3,906,552 | 9/1975 | Weber | 3/21 |
| 4,283,800 | 8/1981 | Wilson | 3/21 |

Primary Examiner—Richard J. Apley
Assistant Examiner—David J. Isabelle
Attorney, Agent, or Firm—Pollock, Vande Sande & Priddy

[57] ABSTRACT

A joint for demountably clamping a tubular member into a main bore in a socket comprises an auxiliary bore directed perpendicular to the axis of the main bore and intersecting it over a small arc and first and second collets that fit in the auxiliary bore. Part cylindrical bearing faces on the collets are shaped to conform to the curvature of the tubular member. A clamping bolt urges the collets together so that they press on the tubular member and retain it in the socket. Preferably a reinforcing insert fits the end of the tubular member and has a disc or annulus that registers with the collets to resist compressive loads on the tube.

4 Claims, 2 Drawing Figures

DEMOUNTABLE JOINT

FIELD OF THE INVENTION

The present invention relates to a demountable joint by which a tube may be clamped into a socket and is a continuation in part of U.S. patent application Ser. No. 386,454 filed June 8, 1982, now abandoned.

SUMMARY OF THE INVENTION

The present invention provides a joint for demountably clamping a tubular member into a main bore in a socket comprising an auxiliary bore directed perpendicular to the axis of the main bore and intersecting it over a small arc, first and second collets which fit in the auxiliary bore and have bearing faces shaped to conform to the curvature of the tubular member, and clamping bolt means for urging the first and second collets together so that they press on the tubular member and retain it in the socket.

The demountable joint combines manufacturing simplicity with ease of assembly and good fatigue life and has the particular advantage that the tubular member need not be weakened by drilling or slitting.

The joint is particularly suitable for clamping a pylon tube to a knee or shin casting in an artificial limb, but is believed to have application outside the artificial limb speciality.

BRIEF DESCRIPTION OF THE DRAWINGS

An embodiment of the invention will now be illustrated in the accompanying drawings in which.

DETAILED DESCRIPTION OF ILLUSTRATED EMBODIMENT

Figure 1:
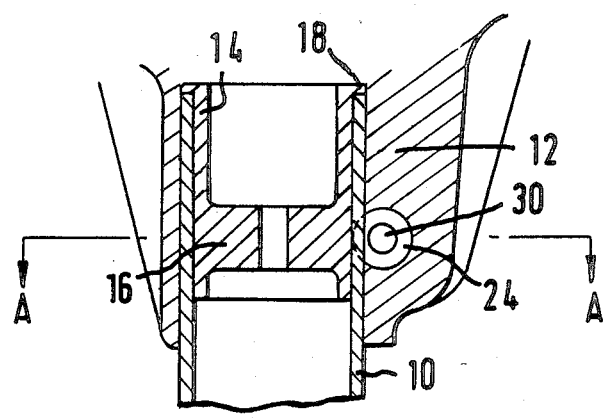
FIG. 1 is a view in vertical section of a demountable joint for fixing pylon tubing into a socket.
Figure 2:
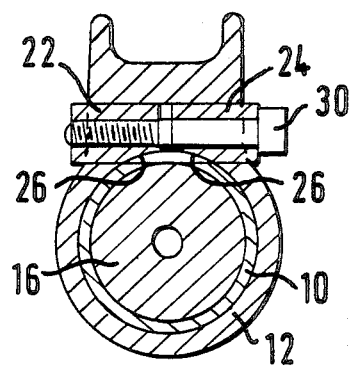
FIG. 2 is a view of the joint in horizontal section on the line A—A of FIG. 1.

In FIG. 1, the upper end of a pylon tube 10 is a push fit in a vertical bore in a socket 12 which is a casting forming part of an artificial limb structure. A reinforcing insert 14 is a push fit into the top of tube 12. It is formed towards its lower end with a horizontally, i.e., transversely directed reinforcing disc or annulus 16 which is capable of withstanding high compressive loads and at its top with an outwardly directed locating flange 18 which acts as an abutment for the top end of the tube 10. As more clearly seen in FIG. 2 the socket 12 is formed with a horizontal bore which intersects the vertical bore in which tube 10 fits over a small arcuate portion thereof. A pair of collets 22, 24 fit into the horizontal bore, one of them 24 having a plain through-hole and the other 22 having a threaded through hole. Each collet has at its inner end a part cylindrical bearing surface 26 whose axis is normal to that of the collet, and which conforms to the curvature of the outer surface of the tube 10 which can only be inserted fully home in the socket 12 when the bearing surfaces 26 are appropriately positioned. It will be noted that in the assembled joint the horizontal bore registers with the transverse annulus 16 of reinforcing insert 14. A clamping bolt 30 is inserted through collet 24 into collet 22 in which it is threadedly located.

To assemble the joint, the insert 14 is placed in the free end of tube 10 which is pushed fully home in the socket 12. The collets 22, 24 are inserted into the horizontal bore and the clamping bolt 30 is inserted and tightened. As it is tightened, the surfaces 26 are clamped into forceful frictional engagement with the external surface of tube 10 and the clamping forces urge the tube 10 against the walls of the bore in socket 12. As a result the tube 10 is held within the socket 12 without the need for the tube 10 to be drilled or slit so that the joint has a very much greater fatigue life than other methods of joining.

Various modifications may be made to the above described embodiment without departing from the invention, the scope of which is defined in the appended claims. For example, the joint has been described in relation to the clamping of pylon tubing, which is normally of a soft metal such as aluminum in a socket in an artificial limb. But although it has been designed with the requirements of artificial limbs in mind, it is believed to be of wide application whenever a length of tubing is to be located in a socket or where two or more lengths of tubing are to be joined by a sleeve or socket. It could be adapted, for example, for the joining together of a tubular steel framework of eg. a chair which is intended to be sold in collapsed state and to be assembled by the purchaser and in such applications could be superior to a conventional screwed joint because of its improved wear-resistance.

I claim:

1. A demountable joint comprising a socket having a blind main bore, a tubular member of soft metal one end of which is inserted into said main bore, an auxiliary bore in the socket directed perpendicular to the axis of said main bore and intersecting it over a small arc, first and second collets which each fit in said auxiliary bore and have at their respective inner ends part cylindrical bearing faces conforming to the curvature of said tubular member, clamping bolt means for urging said first and second collets together so that they press on said tubular member and functionally retain said tubular member in said socket, and a reinforcing insert that is a push fit in said tubular member and has a flange that butts against the end of said main bore and seats on the end of said tubular member that is within the socket to locate said reinforcing insert axially in said tubular member so that it registers with said collets to resist compressive loads on said tubular member.

2. A joint according to claim 1 wherein the reinforcing insert is a flanged tube provided with an internal reinforcing annulus that registers with said collets.

3. A joint according to claim 1 wherein the clamping bolt means passes through a smooth bore in one of said collets and is engaged into a threaded bore in the other of said collets.

4. A joint according to claim 1 wherein said tubular member is a pylon tube of an artificial limb, and said socket is a casting forming part of the artificial limb structure.

* * * * *